(12) United States Patent
Jie et al.

(10) Patent No.: US 11,273,186 B2
(45) Date of Patent: Mar. 15, 2022

(54) APPLICATION OF BACTEROIDES CELLULOSITYCUS IN PREPARING A PREPARATION FOR PREVENTING AND/OR TREATING LIPID METABOLISM RELATED DISEASES

(71) Applicant: BGI SHENZHEN, Shenzhen (CN)

(72) Inventors: Zhuye Jie, Shenzhen (CN); Suisha Liang, Shenzhen (CN); Huihua Xia, Shenzhen (CN); Yuanqiang Zou, Shenzhen (CN); Liang Xiao, Shenzhen (CN); Huijue Jia, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 0 days.

(21) Appl. No.: 16/642,702

(22) PCT Filed: Aug. 29, 2017

(86) PCT No.: PCT/CN2017/099522
§ 371 (c)(1),
(2) Date: Feb. 27, 2020

(87) PCT Pub. No.: WO2019/041141
PCT Pub. Date: Mar. 7, 2019

(65) Prior Publication Data
US 2020/0230181 A1    Jul. 23, 2020

(51) Int. Cl.
| | |
|---|---|
| *A61K 35/741* | (2015.01) |
| *A61K 35/74* | (2015.01) |
| *A23K 50/50* | (2016.01) |
| *A23K 10/18* | (2016.01) |
| *A23L 33/135* | (2016.01) |
| *A61P 9/10* | (2006.01) |
| *A61P 3/06* | (2006.01) |
| *A23C 9/152* | (2006.01) |
| *A23L 2/52* | (2006.01) |
| *A61K 31/702* | (2006.01) |

(52) U.S. Cl.
CPC .............. *A61K 35/74* (2013.01); *A23C 9/152* (2013.01); *A23K 10/18* (2016.05); *A23K 50/50* (2016.05); *A23L 2/52* (2013.01); *A23L 33/135* (2016.08); *A61K 31/702* (2013.01); *A61P 3/06* (2018.01); *A61P 9/10* (2018.01)

(58) Field of Classification Search
CPC .................................................... A61K 35/741
See application file for complete search history.

(56) References Cited

FOREIGN PATENT DOCUMENTS

| | | |
|---|---|---|
| CN | 101945589 A | 1/2011 |
| CN | 105596979 A | 5/2016 |
| CN | 106720938 A | 5/2017 |
| EP | 2889371 A1 | 7/2015 |
| EP | 3202892 A1 | 8/2017 |
| WO | 2015003001 A1 | 1/2015 |
| WO | 2016049826 A1 | 4/2016 |

OTHER PUBLICATIONS

Search Report issued for EP patent application serial No. 17923679.9, dated Mar. 15, 2021.
McNulty, N. P. et al. "Effects of Diet on Resource Utilization by a Model Human Gut Microbiota Containing Bacteroides cellulosilyticus WH2, a Symbiont with an Extensive Glycobiome" PLOS Biology, Aug. 2013, vol. 11, Issue 8, e1001637.
International Search Report issued for PCT/CN2017/099522, dated Jun. 5, 2018.
Written Opinion of the International Searching Authority issued for PCT/CN2017/099522, dated Jun. 5, 2018.

*Primary Examiner* — Rosanne Kosson
(74) *Attorney, Agent, or Firm* — Westman, Champlin & Koehler, P.A.; Z. Peter Sawicki

(57) ABSTRACT

The present invention discloses an application of *Bacteroides cellulosilyticus* in preparing a preparation for preventing and/or treating lipid metabolism related diseases, such as atherosclerosis related diseases, cardiovascular diseases and obesity.

20 Claims, No Drawings

APPLICATION OF BACTEROIDES CELLULOSITYTICUS IN PREPARING A PREPARATION FOR PREVENTING AND/OR TREATING LIPID METABOLISM RELATED DISEASES

CROSS-REFERENCE TO RELATED APPLICATIONS

This application is a US-Phase application based upon PCT Application No. PCT/CN2017/099522 filed with the National Intellectual Property Administration of PRC on Aug. 29, 2017, the entire content of which is incorporated herein by reference.

FIELD

The present disclosure relates to the field of microbiology, in particular to the application of *Bacteroides cellulosilyticus* in preventing and/or treating lipid metabolism related diseases.

BACKGROUND

Atherosclerosis (AS) is the main cause of coronary heart disease, cerebral infarction and peripheral vascular disease, in which lipid metabolism abnormity is the basis of atherosclerotic lesions. The atherosclerosis is characterized by lesions of arteries involved, which are initiated from intima, generally occurring the accumulation of lipids and complex sugars, bleeding and thrombosis, followed by fibrous tissue hyperplasia and calcium deposition, and then gradual metamorphosis and calcification of middle layer of artery which results in thickening and hardening of arterial wall and narrowing of vascular cavity. Once the lesions, always involving in the large and medium-sized muscular arteries, develop enough to block the arterial cavity, the tissues or organs supplied by the arteries will be ischemic or necrotic. The atherosclerosis which is named after the yellow atheromatous appearance of lipid accumulated in the intima of arteries, is caused by combined factors, with complicated pathogenesis. Among them, the main risk factors for atherosclerosis include hypertension, hyperlipidemia and heavy smoking, as well as diabetes, obesity, genetic factors and the like.

Atherosclerotic cardiovascular diseases (ACVD) is the number one killer in developed countries and is increasingly common in developing countries. In recent years, with the rapidly developed economy in our country and significantly improved living standards of people, lifestyles are undergoing profound changes, including accelerated pace of work and life, increased dietary calories and decreased physical activities. Such unhealthy lifestyles result in significant increase on risk factors of cardiovascular diseases (such as obesity and the like), thereby further leading to the rapid increase on incidence of cerebrovascular diseases. For example, diseases such as stroke, myocardial infarction and the like can lead to severe disability, reduced life quality and heavy medical burden. Cardio-cerebrovascular diseases have become the major public health problem in our country in this century due to high morbidity, mortality and disability.

ACVD mainly includes coronary heart disease (CHD), stroke and peripheral arterial diseases. The etiology of ACVD is multifaceted, and many of related factors are associated with lifestyle including smoking, atherosclerotic diet, overweight or obesity, sedentariness, lack of physical activity and the like. The main cause of coronary heart disease is atherosclerosis and the pathological changes of myocardial ischemia and necrosis caused by atherosclerosis. The pathological pathogenesis of coronary heart disease is mainly the increased blood lipids due to lipid metabolism disorder, lipid deposition and infiltration in the inner wall of blood vessel, formation of vascular endothelial foam cells, and chronic inflammatory reactions in blood vessel wall that damage the function and morphology of coronary vascular endothelial cells, formation of vascular endothelial atherosclerotic plaque, further plaque rupture, thrombosis, vascular stenosis or occlusion resulting in coronary blood circulation disorder, myocardial ischemia, damaged myocardial cells, and cardiac insufficiency caused. With the improvement of living standards, the incidence and mortality of coronary heart disease in our country have increased yearly and exhibits a trend of getting younger.

Obesity as a common group of metabolic disorder, is generated by external cause including excess of diet and few activities thus calorie intake exceeding calorie consumption, leading to increase of fat synthesis which is the material basis of obesity; and by internal cause of lipid metabolism disorder. Obese patients have a significantly higher risk (generally 5 to 10 times) of concurrently suffering from coronary heart disease and hypertension than that of non-obese populations, especially for central obese patients with thick waist circumference (male>90 cm and female>85 cm). Obesity can result in cardiac hypertrophy, thickened posterior wall and ventricular septum, cardiac hypertrophy accompanied by increased blood volume, intracellular fluid and intercellular fluid, and increased ventricular end diastolic pressure, pulmonary artery pressure and pulmonary capillary wedge pressure, as well as left ventricular dysfunction and obese cardiomyopathy for some obese populations. Obese patients exhibit significantly increased incidence of sudden death, which may be related to arrhythmia and cardiac ischemia caused by cardiac hypertrophy, and fatty infiltration of the cardiac conduction system.

The treatment for lipid metabolism related diseases especially atherosclerotic cardiovascular diseases (such as coronary heart disease) according to modern medicine mainly includes drug treatment, interventional treatment and surgical treatment.

However, drug treatment often displays toxic and side effects to some degree, and the efficacy of traditional Chinese medicines is not significant effective, with a long treatment cycle and incurability. At present, oral preparations of traditional Chinese medicines for treating coronary heart disease available on market are mainly based on *Salvia miltiorrhiza*, such as drugs with main efficacy of promoting blood circulation, for example GuanXinDanShenPian (including *Salvia miltiorrhiza*, *Panax notoginseng*, Dalbergia wood oil), Danshenpian (including *Salvia miltiorrhiza*), ShuangDanKouFuYe (including *Salvia miltiorrhiza*, cortex of *Paeonia suffruticosa* Andr.), Danqipian (including *Salvia miltiorrhiza*, *Panax notoginseng*), FuFangDanShenPian (including *Salvia miltiorrhiza*, *Panax notoginseng*, Borneol), FuFangDanShenDiWan (including *Salvia miltiorrhiza*, *Panax notoginseng*, Borneol) and the like. Further, some of the drugs as described above contain borneol which has a property of aromatic stimulating, brings consumption of qi and injury of yang, would affect heart function if long-term applied, and stimulates the gastrointestinal tract greatly, thus patients suffering from coronary heart disease as well as gastritis, gastroduodenal lesion or esophagitis, or deficiency cold-type patients are not suitable to use such drugs including borneol. Furthermore, administering the drug FuFang- DanShenPian in a long-term period can cause potassium deficiency symptoms to patients, such as abdominal distension, fatigue and the like.

Interventional and surgical treatments have problems of postoperative restenosis, expensive cost and the like, which cannot resolve the re-precipitation of lipids in blood vessels and form new plaques from the source, thus resulting in narrowing and clogging of blood vessels, and the recurrence of atherosclerotic cardiovascular diseases (such as coronary heart disease) due to poor myocardial blood supply.

Therefore, there is an urgent need in the art to develop a new, non-toxic and non-side effect drug for treating and/or preventing lipid metabolism related diseases, such as atherosclerosis related diseases, cardiovascular diseases and obesity.

SUMMARY

The object of the present disclosure is to provide a new, non-toxic and non-side effect medicine for treating and/or preventing lipid metabolism related diseases.

In a first aspect, the present disclosure in embodiments provides use of *Bacteroides cellulosilyticus* in manufacture of a composition or a preparation for preventing and/or treating lipid metabolism related diseases.

In another preferred embodiment, the lipid metabolism related diseases are selected from the group consisting of atherosclerosis related diseases, cardiovascular diseases, obesity and a combination thereof.

In another preferred embodiment, the strain *Bacteroides cellulosilyticus* is selected from the group consisting of *Bacteroides cellulosilyticus* DSM 14838, *Bacteroides cellulosilyticus* CL02T12C19, *Bacteroides cellulosilyticus* WH2 and a combination thereof.

In another preferred embodiment, the composition is selected from the group consisting of a food composition, a health care composition, a pharmaceutical composition, a beverage composition, a feed composition and a combination thereof.

In another preferred embodiment, the composition is an oral preparation.

In another preferred embodiment, the composition is a liquid preparation, a solid preparation or a semi-solid preparation.

In another preferred embodiment, the dosage form of the composition is selected from the group consisting of powder, pulvis, tablet, sugar coating agent, capsule, granule, suspension, solution, syrup, drop and/or sublingual tablet.

In another preferred embodiment, the food composition includes an emulsion product, a solution product, a powder product or a suspension product.

In another preferred embodiment, the food composition includes dairy, milk powder or emulsion.

In another preferred embodiment, the liquid preparation is selected from the group consisting of a solution product and a suspension product.

In another preferred embodiment, the atherosclerosis related diseases are selected from the group consisting of coronary heart disease, coronary artery disease (CAD), atherosclerotic heart disease, atherosclerotic cardiovascular diseases, ischemic heart disease and a combination thereof.

In another preferred embodiment, the cardiovascular diseases are selected from the group consisting of acute coronary artery syndrome, angina pectoris, arterial sclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemia, dyslipoproteinemia, endothelial dysfunction, familial hypercholesterolemia, familial combined hyperlipidemia, hypo-α-lipoproteinemia, hypertriglyceridemia, hyper-β-lipoproteinemia, hypercholesterolemia, hypertension, hyperlipidemia, intermittent claudication, ischemia, ischemia-reperfusion injury, ischemic heart disease, myocardial ischemia, metabolic syndrome, multiple cerebral infarction dementia, myocardial infarction, obesity, peripheral vascular diseases, reperfusion injury, restenosis, renal atherosclerosis, rheumatic heart disease, stroke, thrombotic disorder, transient ischemic attack and Alzheimer's disease, obesity, diabetes, Syndrome X, impotence, Multiple Sclerosis, Parkinson's disease, inflammatory disorder-related abnormal lipoproteins and a combination thereof.

In another preferred embodiment, the preparation includes a microecological preparation.

In a second aspect, the present disclosure in embodiments provides use of *Bacteroides cellulosilyticus* in manufacture of a composition or a preparation for one or more selected from the group consisting of:

(i) lowering blood lipid level in a mammal;
(ii) reducing body weight of a mammal;
(iii) relieving myocardial ischemia in a mammal; and
(iv) alleviating vascular lesions in a mammal.

In another preferred embodiment, the alleviating vascular lesions in a mammal includes improvement of one or more indicators selected from the group consisting of blood viscosity, blood rheology, blood pressure, blood lipids (such as triglyceride, total cholesterol, high density lipoprotein, low density lipoprotein) and ST segment of electrocardiograph.

In another preferred embodiment, the lowering blood lipid level in a mammal includes reduction of total cholesterol level, triglyceride level, low density lipoprotein level and/or blood viscosity level in the blood.

In another preferred embodiment, the reducing body weight of a mammal indicates that the weight of mammal in an experimental group is reduced by at least 10%, preferably 15% to 20%, compared to that in a model group.

In another preferred embodiment, the relieving myocardial ischemia in a mammal includes reducing ST segment displacement of myocardial ischemia in the mammal.

In another preferred embodiment, the mammal includes human or non-human mammal.

In another preferred embodiment, the non-human mammal includes rodents, such as rats and mice.

In a third aspect, the present disclosure in embodiments provides a composition for use in treating and/or preventing cardiovascular diseases, comprising:

(a) a safe and effective amount of *Bacteroides cellulosilyticus*; and
(b) a food or pharmaceutically acceptable carrier.

In a fourth aspect, the present disclosure in embodiments provides a composition for use in preventing and/or treating obesity, comprising:

(a) a safe and effective amount of *Bacteroides cellulosilyticus*; and
(b) a food or pharmaceutically acceptable carrier.

In a fifth aspect, the present disclosure in embodiments provides a composition for use in treating and/or preventing atherosclerosis related diseases, comprising:

(a) a safe and effective amount of *Bacteroides cellulosilyticus*; and
(b) a food or pharmaceutically acceptable carrier.

In a sixth aspect, the present disclosure in embodiments provides a composition for use in treating and/or preventing lipid metabolism related diseases, comprising:

(a) a safe and effective amount of *Bacteroides cellulosilyticus*; and (b) a food or pharmaceutically acceptable carrier.

In another preferred embodiment, the strain *Bacteroides cellulosilyticus* is selected from the group consisting of *Bacteroides cellulosilyticus* DSM 14838, *Bacteroides cellulosilyticus* CL02T12C19, *Bacteroides cellulosilyticus* WH2 and a combination thereof.

In another preferred embodiment, the composition further contains a growth factor, preferably a milk growth factor.

In another preferred embodiment, the composition is selected from the group consisting of a food composition, a health care composition, a pharmaceutical composition, a beverage composition, a feed composition and a combination thereof.

In another preferred embodiment, the composition is an oral preparation.

In another preferred embodiment, the composition is a liquid preparation, a solid preparation or a semi-solid preparation.

In another preferred embodiment, the dosage form of the composition is selected from the group consisting of powder, pulvis, tablet, sugar coating agent, capsule, granule, suspension, solution, syrup, drop, sublingual tablet and a combination thereof.

In another preferred embodiment, the food composition includes an emulsion product, a solution product, a powder product or a suspension product.

In another preferred embodiment, the food composition includes dairy, milk powder or emulsion.

In another preferred embodiment, the liquid preparation is selected from the group consisting of a solution product and a suspension product.

In another preferred embodiment, the composition contains $10$-$1 \times 10^{15}$ cfu/mL or cfu/g of *Bacteroides cellulosilyticus*, preferably $1 \times 10^{4}$-$1 \times 10^{10}$ cfu/mL or cfu/g of *Bacteroides cellulosilyticus*, based on the total volume or total weight of the composition.

In another preferred embodiment, the composition contains 0.0001 wt % to 99 wt %, preferably 0.1 wt % to 90 wt % of *Bacteroides cellulosilyticus*, based on the total weight of the composition. In another preferred embodiment, the composition is in a unit dosage form, i.e., one tablet, one capsule or one vial, and the composition in each unit dosage form is of a mass of 0.05 g to 5 g, preferably 0.1 g to 1 g.

In another preferred embodiment, the composition further contains probiotics and/or prebiotics.

In another preferred embodiment, the probiotics are selected from the group consisting of Lactic acid bacteria, *Bifidobacteria, Lactobacillus acidophilus* and a combination thereof.

In another preferred embodiment, the prebiotics are selected from the group consisting of fructooligosaccharide (FOS), galactooligosaccharide (GOS), xylooligosaccharide (XOS), lactosucro se (LACT), soybean oligosaccharides (SOS), Inulin, oligosaccharide and a combination thereof.

In another preferred embodiment, the composition further contains a substance capable of maintaining the viability of *Bacteroides cellulosilyticus*, such as a protective agent.

In another preferred embodiment, the substance capable of maintaining the viability of *Bacteroides cellulosilyticus* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof.

In another preferred embodiment, the substance capable of maintaining the viability of *Bacteroides cellulosilyticus* such as a protective agent is of a weight ratio (wt %) of 0.1% to 2%, preferably 0.5% to 1.5%, more preferably 0.5% to 1.0%, based on the total weight of the composition.

In another preferred embodiment, the substance capable of maintaining the viability of *Bacteroides cellulosilyticus* such as a protective agent is of an amount of 1 mg to 20 mg, preferably 5 mg to 15 mg, more preferably 5 mg to 10 mg, based on 1 g of the composition.

In a seventh aspect, the present disclosure in embodiments provides a method for preparing the composition as defined in any of the third aspect to the sixth aspect of the present disclosure, comprising the step of:

mixing (i) the *Bacteroides cellulosilyticus* with (ii) a food or pharmaceutically acceptable carrier to form the composition as defined in any of the third aspect to the sixth aspect of the present disclosure.

In another preferred embodiment, the composition further contains a substance capable of maintaining the viability of *Bacteroides cellulosilyticus*, such as a protective agent.

In another preferred embodiment, the substance capable of maintaining the viability of *Bacteroides cellulosilyticus* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof.

In another preferred embodiment, the composition is an oral preparation.

In an eighth aspect, the present disclosure in embodiments provides a method for relieving myocardial ischemia in a mammal, comprising the step of:

administering the composition as defined in any of the third aspect to the sixth aspect of the present disclosure to a subject, thereby relieving myocardial ischemia in the mammal.

In another preferred embodiment, the composition is administrated orally.

In another preferred embodiment, the administration dosage is 0.01 to 5 g/50 kg body weight per day, preferably 0.1 to 2 g/50 kg body weight per day.

In another preferred embodiment, the subject includes human and non-human mammal.

In another preferred embodiment, the non-human mammal includes rodents such as mice and rats, and primates such as monkeys.

In another preferred embodiment, the method is non-therapeutic or non-diagnostic.

In a ninth aspect, the present disclosure in embodiments provides a method for reducing blood lipids and body weight in a mammal, comprising the step of:

administering the composition as defined in any of the third aspect to the sixth aspect of the present disclosure to a subject, thereby reducing blood lipids and body weight in the mammal.

In another preferred embodiment, the composition is administrated orally.

In another preferred embodiment, the administration dosage is 0.01 to 5 g/50 kg body weight per day, preferably 0.1 to 2 g/50 kg body weight per day.

In another preferred embodiment, the subject includes human and non-human mammal.

In another preferred embodiment, the non-human mammal includes rodents such as mice and rats, and primates such as monkeys.

In another preferred embodiment, the method is non-therapeutic or non-diagnostic.

In a tenth aspect, the present disclosure in embodiments provides a method for alleviating vascular lesions in a mammal, comprising the step of:

administering the composition as defined in any of the third aspect to the sixth aspect of the present disclosure to a subject, thereby alleviating vascular lesions in the mammal.

In another preferred embodiment, the composition is administrated orally.

In another preferred embodiment, the administration dosage is 0.01 to 5 g/50 kg body weight per day, preferably 0.1 to 2 g/50 kg body weight per day.

In another preferred embodiment, the subject includes human and non-human mammal.

In another preferred embodiment, the method is non-therapeutic or non-diagnostic.

In an eleventh aspect, the present disclosure in embodiments provides a method for treating and/or preventing lipid metabolism related diseases, comprising the step of:

administering the composition as defined in any of the third aspect to the sixth aspect of the present disclosure to a subject, thereby treating and/or preventing lipid metabolism related diseases.

In another preferred embodiment, the composition is administrated orally.

In another preferred embodiment, the administration dosage is 0.01 to 5 g/50 kg body weight per day, preferably 0.1 to 2 g/50 kg body weight per day.

In another preferred embodiment, the subject includes human and non-human mammal.

In another preferred embodiment, the method is non-therapeutic or non-diagnostic.

It should be understood that, the technical features of the present disclosure as described above and the technical features as specifically described below (such as examples) may be combined with each other to form a new or preferred technical solution within the scope of the present disclosure, which will not be repeated due to limited space.

DETAILED DESCRIPTION

Present inventors have surprisingly discovered that strain *Bacteroides cellulosilyticus* exhibits the efficacy of preventing and/or treating lipid metabolism related diseases such as atherosclerosis related diseases, cardiovascular diseases, obesity and the like, after extensive and intensive researches and experiments. Experiments have shown that the active composition containing *Bacteroides cellulosilyticus* is capable of significantly reducing body weight, lowering blood lipids, relieving myocardial ischemic diseases (such as reducing myocardial ischemic ST segment displacement in a mammal) and alleviating vascular lesions through feeding experimental subjects. On this basis, the present inventors have completed the present disclosure.

As used herein, the term "comprising" means that various components can be applied together in a mixture or a composition of the present disclosure. Accordingly, the terms "essentially consisting of . . . " and "consisting of . . . " are included in the scope of the term "comprising".

As used herein, the term "growth factor" includes a milk growth factor, specifically including nutrients of vitamins, purines, pyrimidines and a combination thereof.

In which, the vitamins include but are not limited to Vitamin C, Vitamin E, Vitamin A, Vitamin A precursor, Vitamin $B_6$, Vitamin $D_3$, Vitamin K, folic acid and a combination thereof;

the purines include but are not limited to purine nucleosides, which include 5'-phosphate esters of purine nucleosides; the 5'-phosphate esters of purine nucleosides are selected from the group consisting of inosinic acid (inosine-5'-phosphate ester; IMP), guanylic acid (guanosine-5'-phosphate ester; GMP), xanthylic acid (xanthine-5'-phosphate ester; XMP), adenylic acid (adenosine-5'-phosphate ester; AMP) and a combination thereof; and the pyrimidines include all substances containing a pyrimidine structure.

As used herein, the terms "lowering body weight of a mammal" and "controlling weight gain in a mammal" can be used interchangeably and refer to the treatment of symptoms of weight gain caused by obesity.

As used herein, the term "alleviating vascular lesions in a mammal" refers to the treatment of symptoms of vascular lesions caused by atherosclerosis.

In the present disclosure, the alleviating vascular lesions in a mammal includes improvement of one or more indicators selected from the group consisting of blood viscosity, blood rheology, blood lipids (mainly triglyceride, total cholesterol, high density lipoprotein and low density lipoprotein) and ST segment of electrocardiograph.

Myocardial Ischemic ST Segment Displacement

As used herein, the term "myocardial ischemic ST segment displacement" means that myocardial ischemia can be diagnosed by an electrocardiogram, mainly reflected as ST segment depression or elevation.

*Bacteroides cellulosilyticus* of the Present Disclosure and Application Thereof As used herein, the "*Bacteroides cellulosilyticus* of the present disclosure" is a kind of strict anaerobe, which is non-motile and rod-like, and has a length of 1.7 μm and a width of 0.9 μm. The *Bacteroides cellulosilyticus* is Gram-negative, has cytoderm ultra-structure, and does not form heat-resistant spore, the model bacterium of which is isolated from human feces (referring to Robert C, Chassard C, Lawson P A, et al. *Bacteroides cellulosilyticus* sp. nov., a cellulolytic bacterium from the human gut microbial community[J]. International journal of systematic and evolutionary microbiology, 2007, 57(7): 1516-1520).

In a preferred embodiment, the *Bacteroides cellulosilyticus* is selected from the group consisting of *Bacteroides cellulosilyticus* DSM 14838, *Bacteroides cellulosilyticus* CL02T12C19, *Bacteroides cellulosilyticus* WH2 and a combination thereof.

The present disclosure in embodiments provides use of *Bacteroides cellulosilyticus* in preventing and/or treating lipid metabolism related diseases, such as atherosclerosis related diseases, cardiovascular diseases, obesity and the like. The *Bacteroides cellulosilyticus* of the present disclosure is capable of:

(i) lowering blood lipid level in a mammal;
(ii) reducing body weight of a mammal;
(iii) relieving myocardial ischemia in a mammal; and/or
(iv) alleviating vascular lesions in a mammal.

According to a preferred embodiment of the present disclosure, Sprague-Dawley (SD) rats are used as experimental rats and are fed with high-fat feed for hyperlipidemia modeling, thus obtaining hyperlipidemic rat models. The hyperlipidemic rat models treated with *Bacteroides cellulosilyticus* have showed significantly reduced body weight and significantly reduced levels of indicators associated with diseases such as atherosclerosis related diseases, cardiovascular diseases, obesity and the like, for example, blood lipid level, total cholesterol level, triglyceride level, low density lipoprotein level and blood viscosity level, compared to the untreated model control group (model group).

According to another preferred embodiment of the present disclosure, Sprague-Dawley (SD) rats are used as experimental rats and are treated with pituitrin. The pituitrin-treated SD rats after administrated with *Bacteroides cellulosilyticus*, have showed significantly reduced levels of indicators associated with cardiovascular diseases (myocardial ischemic ST segment displacement), compared to the untreated model control group (model group).

Therefore, the *Bacteroides cellulosilyticus* of the present disclosure is capable of preventing and/or treating lipid metabolism related diseases, such as atherosclerosis related diseases, cardiovascular diseases, obesity and the like.

Composition and Application Thereof

The present disclosure in embodiments also provides a composition. Preferably, the composition includes a food composition, a health care composition, a pharmaceutical composition, a beverage composition or a feed composition. More preferably, the composition is a pharmaceutical composition. The composition contains (i) an effective amount of *Bacteroides cellulosilyticus*; and (ii) a pharmaceutically acceptable carrier.

In a preferred embodiment, the composition further contains a growth factor, such as a milk growth factor. In a preferred embodiment, the composition further contains probiotics selected from the group consisting of Lactic acid bacteria, *Bifidobacteria, Lactobacillus acidophilus* and a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide and a combination thereof.

In a preferred embodiment, the composition further contains a substance capable of maintaining the viability of *Bacteroides cellulosilyticus* (such as a protective agent), which includes cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof. The substance capable of maintaining the viability of *Bacteroides cellulosilyticus* (such as a protective agent) is of a weight ratio of 0.1% to 2%, preferably 0.5% to 1.5%, more preferably 0.5% to 1.0%, based on the total weight of the composition.

In a preferred embodiment, the composition is a liquid preparation, a solid preparation or a semi-solid preparation.

In a preferred embodiment, the liquid preparation is selected from the group consisting of a solution product and a suspension product.

In a preferred embodiment, the dosage form of the composition is selected from the group consisting of powder, pulvis, tablet, sugar coating agent, capsule, granule, suspension, solution, syrup, drop and/or sublingual tablet.

The composition of the present disclosure may be administered in any form of oral solution, tablet, injection, orally disintegrating tablet, lyophilized powder and capsule, preferably in the dosage form of enteric agent (such as capsule). In the present disclosure, the excipient, pharmaceutically acceptable vehicle and carrier used in the present disclosure are mainly selected depending on the property suitable for the bacteria or metabolites thereof and the specific administration means required, which is beneficial to the smooth passage of the bacteria or metabolites thereof through stomach thus absorbed by the administrated subject, without special indication. These substances can be selected according to the administration route.

The composition of the present disclosure may further contain any additional excipients among those commonly used in pharmaceutical preparations, for example, for stabilization of the composition itself, or allowing to be easily dispersed or imparting a suitable taste.

Among the excipients, suitable examples are inulin, fructose, starch, xylooligosaccharide, silicon dioxide, buffering agent and flavoring agent.

The pharmaceutical preparation of the present disclosure may further contain an auxiliary active component.

Lactose, maltodextrin, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, mineral oil and the like can be all used as carriers, excipients or diluents of the pharmaceutical composition in the present disclosure.

Further, the pharmaceutical composition of the present disclosure may further contain lubricant, wetting agent, emulsifier, suspension stabilizer, preservative, sweetening agent, flavor and the like. The pharmaceutical composition of the present disclosure can be produced in an enteric coating preparation via a variety of well-known methods, so that the active component of the pharmaceutical composition (i.e., the microorganism) can pass through stomach smoothly without destroyed by gastric acid.

Further, the microorganism of the present disclosure may be used in the form of capsule prepared by conventional methods. For example, standard excipients and lyophilized microorganism of the present disclosure are mixed to prepare pills which are subsequently dispensed into gelatin capsules. In addition, the microorganism of the present disclosure and pharmaceutically acceptable excipients (such as liquid gum, cellulose, silicate, mineral oil or the like) can be mixed and prepared in suspension or dispersion, and such a suspension or dispersion can be filled into soft gelatin capsules.

The pharmaceutical composition of the present disclosure can be prepared in enteric coating tablets for oral use. The term "enteric coating" in the present disclosure includes all coatings that are allowed for conventional drugs. These coatings are not degraded by gastric acid, however, can be completely broken down in small intestine and then quickly release the microorganism of the present disclosure. The enteric coating of the present disclosure can be maintained in a HCl solution for gastric acid synthesis (such as pH=1) at 36° C. to 38° C. for more than 2 hours, preferably broken down in a buffer solution for intestinal fluid synthesis (such as pH=7) within one hour.

The enteric coating of the present disclosure is coated in an amount of about 16 to 30 mg per tablet, preferably 16 to 25 mg per tablet, and more preferably 16 to 20 mg per tablet. The thickness of the enteric coating in the present disclosure is 5 to 100 μm, ideally 20 to 80 μm. The components of enteric coating are selected from conventional polymers which are known in public.

The preferred enteric coating of the present disclosure is prepared by a copolymer of cellulose acetate phthalate polymer or cellulose acetate trimellitate polymer and methacrylic acid, for example, a copolymer of methacrylic acid and methylcellulose hydroxypropyl phthalate or its ester derivatives, in which the amount of methacrylic acid is more than 40%.

The cellulose acetate phthalate used in the enteric coating of the present disclosure has a viscosity of about 45 to 90 cp, an acetyl content of 17 to 26%, and a phthalic acid content of 30 to 40%. The cellulose acetate trimellitate used in the enteric coating has a viscosity of about 5 to 21 cp, and an acetyl content of 17 to 26%. Cellulose acetate trimellitate, produced by Eastman Kodak Company, can be used as the enteric coating material in the present disclosure.

The hydroxypropyl methyl cellulose phthalate used in the enteric coating of the present disclosure generally has a molecular weight of 20,000 to 130,000 Daltons (ideally 80,000 to 100,000 Daltons), a hydroxypropyl content of 5 to 10%, a methoxyl content of 18 to 24% and a phthaloyl content of 21 to 35%.

The hydroxypropyl methyl cellulose phthalate used in the enteric coating of the present disclosure is HP50, produced by Shin-Etsu Chemical Co. Ltd. of Japan. HP50 contains 6 to 10% of hydroxypropyl, 20 to 24% of methoxy and 21 to 27% of propyl; with a molecular weight of 84,000 Daltons. Another enteric coating material is HP55, which contains 5 to 9% of hydroxypropyl, 18 to 22% of methoxy and 27 to 35% of phthalic acid, with a molecular weight of 78,000 Daltons.

The enteric coating of the present disclosure is prepared by spraying the enteric coating solution onto the core through conventional methods. Solvents for the enteric coating method are alcohols (such as ethanol), ketones (such as acetone), halogenated hydrocarbon compounds (such as dichloromethane) or a combination thereof. Softeners such as di-n-butyl phthalate and glyceryl triacetate are added to the enteric coating solution in a ratio of 1 part of the coating to about 0.05 parts (or about 0.3 parts) of the softener. The spraying method is preferably performed continuously, and the amount of spray material can be controlled according to the conditions for coating. The spray pressure can be adjusted flexibly, generally, an average pressure of 1 to 1.5 Pa will result in ideal results.

The "pharmacologically effective amount" in the specification refers to an amount which is functional or active to human and/or animals and is acceptable to human and/or animals. For example, a preparation containing $10$-$1\times10^{20}$ cfu/ml or cfu/g (particularly $1\times10^{4}$-$1\times10^{15}$ cfu/ml or cfu/g, more particularly $1\times10^{6}$-$1\times10^{11}$ cfu/ml or cfu/g) of *Bacteroides cellulosilyticus* can be prepared in the present disclosure.

When the *Bacteroides cellulosilyticus* is used in the manufacture of pharmaceutical composition, the effective dosage of *Bacteroides cellulosilyticus* used may vary depending on the administration route and the severity of disease to be treated. A dosage form suitable for internal administration includes about $10$-$1\times10^{20}$ cfu/ml or cfu/g (particularly $1\times10^{4}$-$1\times10^{15}$ cfu/ml or cfu/g, more particularly $1\times10^{6}$-$1\times10^{11}$ cfu/ml or cfu/g) of *Bacteroides cellulosilyticus* or its active component produced by fermentation, which is mixed with a solid or liquid pharmaceutically acceptable carrier. This dosage regimen can be adjusted to provide the best therapeutic response. For example, several divided doses may be administrated daily, or the dosage may be proportionally reduced according to the urgent need of treatment condition.

The *Bacteroides cellulosilyticus* may be administered by oral route and the like. Solid carriers include starch, lactose, dicalcium phosphate, microcrystalline cellulose, sucrose and white clay; and liquid carriers include culture medium, polyethylene glycol, non-ionic surfactants and edible oils (such as corn oil, peanut oil and sesame oil), as long as they are suitable for the property of *Bacteroides cellulosilyticus* and the specific administration means required. Adjuvants commonly used in the manufacture of pharmaceutical composition may also be advantageously included, for example, flavoring agents, pigments, preservatives and antioxidants such as Vitamin E, Vitamin C, BHT and BHA.

From the standpoint of ease of manufacture and administration, preferred pharmaceutical composition is the solid composition, especially tablets and solid-filled or liquid-filled capsules. Preferred is oral administration.

The composition of the present disclosure is administered to individuals once or several times per day. The administration dosage unit refers to a dosage that is physically separated and suitable for application in human or all individuals of other mammals. Each unit contains a pharmaceutically acceptable carrier and a therapeutically effective amount of microorganism of the present disclosure. The administration dosage varies with the severity of lipid metabolism related diseases in patients (such as atherosclerosis related diseases, cardiovascular diseases, obesity and the like), the contained supplementary active components and the microorganism used. Further, if possible, the composition can be administered separately and continuously as necessary. Therefore, the administration dosage does not limit the scope of the present disclosure. In addition, the "composition" in the present disclosure means not only a medicament but also a functional food or a health supplement food. In a preferred embodiment, the composition includes beverage, food, medicine, animal feed and the like.

In a preferred embodiment, the present disclosure provided is a food composition, which contains an effective amount of *Bacteroides cellulosilyticus* as well as a food acceptable carrier as balance. The dosage form of the food composition is selected from a solid product, a dairy product, a solution product, a powder product and a suspension product. In a preferred embodiment, the food composition may further contain a growth factor, such as a milk growth factor. In a preferred embodiment, the composition further contains probiotics selected from the group consisting of Lactic acid bacteria, *Bifidobacteria, Lactobacillus acidophilus* and a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide and a combination thereof. In a preferred embodiment, the composition further contains a substance capable of maintaining the viability of *Bacteroides cellulosilyticus* (such as a protective agent), including cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof.

In a preferred embodiment, the composition has the following formula:

$10$-$1\times10^{20}$ cfu/mL of *Bacteroides cellulosilyticus*; and
a food or pharmaceutically acceptable carrier and/or excipient.

In another preferred embodiment, the composition has the following formula:

$1\times10^{6}$-$1\times10^{11}$ cfu/mL of *Bacteroides cellulosilyticus*; and
a food or pharmaceutically acceptable carrier and/or excipient.

Microecological Preparation

Microecological preparation is a biological preparation containing probiotics or metabolites thereof or a dietary supplement that can supply probiotics, which are capable of adjusting and maintaining the microecological balance in intestine, thus achieving the purpose of improving human health. The microecological preparation mainly includes probiotics, prebiotics and synbiotics.

In the present disclosure, the microecological preparation contains (a) a safe and effective amount of *Bacteroides cellulosilyticus*; and (b) a food acceptable carrier or a pharmaceutically acceptable carrier. In a preferred embodiment, the preparation further contains a growth factor, such as a milk growth factor, preferably including vitamins, purines and/or pyrimidines. In a preferred embodiment, the preparation further contains probiotics selected from the group consisting of Lactic acid bacteria, *Bifidobacteria*, *Lactobacillus acidophilus* and a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide and a combination thereof. In a preferred embodiment, the composition further contains a substance capable of maintaining the viability of *Bacteroides cellulosilyticus* (such as a protective agent) selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof.

Culture of *Bacteroides cellulosilyticus*

In the present disclosure, *Bacteroides cellulosilyticus* is anaerobically cultured in a minced meat culture medium (DSMZ Medium 78) at 37° C. for 48 to 72 hours.

Method for Relieving Myocardial Ischemia in a Mammal

In another preferred embodiment, the method includes ingesting a pharmaceutical composition, a food composition, a beverage composition or a combination thereof of the present disclosure. The subject for experiments includes mammals, such as human.

In another preferred embodiment, the method includes ingesting a pharmaceutical composition, a food composition, an animal feed or a combination thereof of the present disclosure. The subject for experiments includes animals, preferably mice or rabbit.

Method for Reducing Blood Lipids and Body Weight in a Mammal

In another preferred embodiment, the method includes ingesting a pharmaceutical composition, a food composition, a beverage composition or a combination thereof of the present disclosure. The subject for experiments includes mammals, such as human.

In another preferred embodiment, the method includes ingesting a pharmaceutical composition, a food composition, an animal feed or a combination thereof of the present disclosure. The subject for experiments includes animals, preferably mice or rabbit.

Method for Alleviating Vascular Lesions in a Mammal

In another preferred embodiment, the method includes ingesting a pharmaceutical composition, a food composition, a beverage composition or a combination thereof of the present disclosure. The subject for experiments includes mammals, such as human.

In another preferred embodiment, the method includes ingesting a pharmaceutical composition, a food composition, an animal feed or a combination thereof of the present disclosure. The subject for experiments includes animals, preferably mice or rabbit.

Method for Treating and/or Preventing Lipid Metabolism Related Diseases

In another preferred embodiment, the method includes ingesting a pharmaceutical composition, a food composition, a beverage composition or a combination thereof of the present disclosure. The subject for experiments includes mammals, such as human.

In another preferred embodiment, the method includes ingesting a pharmaceutical composition, a food composition, an animal feed or a combination thereof of the present disclosure. The subject for experiments includes animals, preferably mice or rabbit.

The advantages of the present disclosure mainly include the followings:

(a) *Bacteroides cellulosilyticus* of the present disclosure is capable of significantly treating and/or preventing lipid metabolism related diseases, such as atherosclerosis related diseases, cardiovascular diseases, obesity and the like.

(b) *Bacteroides cellulosilyticus* of the present disclosure is capable of significantly reducing body weight and blood lipids, such as reducing total cholesterol level, triglyceride level, low density lipoprotein level and blood viscosity level.

(c) *Bacteroides cellulosilyticus* of the present disclosure is capable of significantly relieving myocardial ischemia.

(d) *Bacteroides cellulosilyticus* of the present disclosure is capable of significantly alleviating vascular lesions.

(e) *Bacteroides cellulosilyticus* of the present disclosure shows significantly therapeutic effect, with few toxic and side effects and greatly reduced cost.

The present disclosure is further described below with reference to specific embodiments. It should be understood that these examples are only for illustrating the present disclosure and not intended to limit the scope of the present disclosure. The conditions of experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise specified, the materials and agents used in the examples are all commercially available products.

TongMaiJiangZhiPian is produced by Jilin Baixingtang Pharmaceutical Co., Ltd., with an approval number of Z22024984.

FuFangDanShenPian is produced by Tianjin Tianshili (Liaoning) Pharmaceutical Co., Ltd., with an approval number of Z21020381.

Example 1: Therapeutic Effect of *Bacteroides cellulosilyticus* in a Hyperlipidemic Rat Model

*Bacteroides cellulosilyticus* DSM 14838 (bacterial agent 1) was purchased from DSMZ (Leibniz-Institut DSMZ-Deutsche Sammlung von Mikroorganismen and Zellkulturen GmbH). *Bacteroides cellulosilyticus* CL02T12C19 (bacterial agent 2) was obtained from Harvard Medical School, Coyne M J, Zitomersky N L, McGuire A M, et al. Evidence of extensive DNA transfer between bacteroidales species within the human gut [J]. MBio, 2014, 5(3): e01305-14. *Bacteroides cellulosilyticus* WH2 (bacterial agent 3) was obtained from the Medicine School of Washington University, Effects of diet on resource utilization by a model human gut microbiota containing *Bacteroides cellulosilyticus* WH2, a symbiont with an extensive glycobiome [J]. PLoS biology, 2013, 11(8): e1001637. The bacterial agents were respectively anaerobically cultured in a minced meat culture medium (DSMZ Medium 78) at 37° C. for 48 to 72 hours. Experiments were started after identification through 16S rDNA sequencing. Table 1 shows the strain information.

TABLE 1

| Nos: | Name of Strain |
| --- | --- |
| Bacterial agent 1 | *Bacteroides cellulosilyticus* DSM 14838 |
| Bacterial agent 2 | *Bacteroides cellulosilyticus* CL02T12C19 |
| Bacterial agent 3 | *Bacteroides cellulosilyticus* WH2 |

Strain information

Sprague-Dawley (SD) rats purchased from Guangdong Medical Laboratory Animal Center were used in the experiment. The SD rats were 6-week old rats and fed normally in the environment of Specific pathogen Free (SPF) level. Total of 70 SD rats were purchased, and fed adaptively for 1 week, followed by randomly divided into 6 groups, including a model control group, bacterial agent group 1, bacterial agent group 2, bacterial agent group 3, TongMaiJiangZhiPian group (the TongMaiJiangZhiPian, a positive drug for treating hyperlipidemia) and a normal control group, 10 rats for each group. The bacterial agent group 1, the bacterial agent group 2, the bacterial agent group 3, the TongMaiJiangZhiPian group and the model control group after divided were respectively fed with high-fat feed for construction of hyperlipidemia model, in which the high-fat feed for hyperlipidemia modeling includes 78.8% of basic feed, 1% cholesterol, 10% egg yolk powder, 10% lard oil and 0.2% bile salt, purchased from Trophic Animal Feed High-Tech Co. Ltd, Nantong; and the normal control group was fed with ordinary feed purchased from Guangdong Medical Laboratory Animal Center. The experiment was conducted through the combination of modeling and intervention, in which the concentration of prepared active bacteria for the bacterial agent group 1, the bacterial agent group 2 and the bacterial agent group 3 was $10^9$ cfu/ml, and the administration dosage for TongMaiJiangZhiPian group was 0.6 g/kg per day. The bacteria solution was replaced with fresh culture medium every other day to prevent inactivation or death of bacteria. The bacteria solution was stored at 4° C. under an anaerobic condition. When the experiment was started, the related rats were fed with the high-fat feed while intervened with bacterial agents. Specifically, the bacterial agent group 1, the bacterial agent group 2 and the bacterial agent group 3 were administrated intragastrically with 2 ml of bacterial solution per day, the model control group was administrated intragastrically with 2 ml of phosphate buffer saline (PBS) per day, and the TongMaiJiangZhiPian group was administrated with the drug TongMaiJiangZhiPian in an amount of 0.6 g/kg per day. The rats were recorded with data including body weight, physical conditions, food-intake amount and the like weekly before and after the modeling and the intervention. After the completion of experiment, the rats were sacrificed, in which fat content was recorded, and serum was collected for measuring the content of blood lipids in serum with reference to the kit instruction, including total cholesterol (TC), triglyceride (TG), high density lipoprotein (HDLC) and low density lipoprotein (LDLC). Rat blood was collected at carotid artery before the sacrifice of rats for detection of hemorheology.

Experimental results were as below.

1. Effect of Probiotics on Body Weight of Hyperlipidemia Model Rats

TABLE 2

Effects of bacterial agents 1, 2 and 3 on body weight of obese rats

| Experimental group(s) | week 0 | week 3 | week 5 | week 7 | week 9 |
| --- | --- | --- | --- | --- | --- |
| Model group | 92.8 ± 4.8 | 125.86 ± 5.0 | 269.4 ± 6.1 | 322.5 ± 7.8 | 434.27 ± 10.9 |
| Bacterial agent group 1 | 91.7 ± 4.9 | 116.8 ± 6.4 | 239.5 ± 6.9 | 287.2 ± 8.2* | 359.2 ± 9.9** |
| Bacterial agent group 2 | 92.9 ± 5.2 | 120.7 ± 6.0 | 240.2 ± 7.1 | 289.1 ± 8.0* | 361.8 ± 9.6** |
| Bacterial agent group 3 | 91.8 ± 6.0 | 118.6 ± 6.8 | 238.8 ± 7.4 | 280.2 ± 8.7* | 351.4 ± 10.3** |
| TongMaiJiangZhiPian group | 92.3 ± 5.8 | 121.4 ± 6.1 | 243.4 ± 7.0 | 290.5 ± 7.6* | 380 ± 9.8* |
| Normal group | 93.01 ± 5.6 | 111.68 ± 5.9 | 156.0 ± 6.0▲ | 227.0 ± 8.2▲▲ | 282.5 ± 9.6▲▲▲ |

The data in Table 2 show that the body weight of rats is gradually increased with the progress of experiment. In which, the weight gain of all rats fed with high fat is higher than that of rats in the normal group; the body weight of the normal group is significantly lower than that of the model group at week 5 (▲$P<0.05$); and the weight difference between the normal group and the model group is enlarged significantly at week 9 (▲▲▲$P<0.0001$). The body weight of rats in the bacterial agent groups (bacterial agent groups 2 and 3) began to differ with that of the model group at week 7 (*$P<0.05$); and the body weight of rats in the three bacterial agent groups differs with that of the model group more significantly at week 9 (**$P<0.01$). All bacterial agent groups show a superior efficacy than that of TongMaiJiangZhiPian group, indicating that the intervention of bacterial agents 1, 2 and 3 can effectively control the weight gain of rats.

2. Effect of Probiotics on Blood Lipids in Obese Rat Model

TABLE 3

Effect of bacterial agents 1, 2 and 3 on blood lipids of obese rats

| Experimental group(s) | Total cholesterol (TC) (mmol/L) | Triglyceride (TG) (mmol/L) | Low density lipoprotein (LDLC) (mmol/L) | High density lipoprotein (HDLC) (mmol/L) | Blood viscosity (mPa · s) |
|---|---|---|---|---|---|
| Model group | 5.621 | 4.205 | 2.479 | 0.326 | 2.32 |
| Bacterial agent group 1 | 2.918* | 1.987* | 1.832* | 0.414 | 1.29* |
| Bacterial agent group 2 | 3.078* | 1.014* | 1.769* | 0.397 | 1.41* |
| Bacterial agent group 3 | 2.832* | 1.953* | 1.859* | 0.327 | 1.38* |
| TongMaiJiangZhiPian group | 3.187* | 1.982* | 1.798* | 0.357 | 1.45* |
| Normal group | 3.527* | 1.852* | 1.431** | 0.251 | 1.01* |

The results in Table 3 show that the intervention of bacterial agents 1, 2 and 3 can effectively control the levels of TC, TG, LDLC and blood viscosity in blood relative to the model group (*P<0.05), and the bacterial agent groups 1, 2 and 3 exhibit a better effect than the TongMaiJiangZhiPian group. It is known that the main components of blood lipids are cholesterol and triglyceride, and the increase of cholesterol and triglyceride levels in plasma is closely related to the occurrence of atherosclerosis. The bacterial agents 1, 2 and 3 are all capable of reducing blood lipids and significantly reducing blood viscosity, thereby effectively preventing the blood from being in a highly viscous and hypercoagulable state, improving hemorheology and alleviating vascular lesions. Therefore, bacterial agents 1, 2 and 3 can reduce the levels of indicators associated with atherosclerosis related diseases and cardiovascular diseases.

Example 2: Effect of *Bacteroides cellulosilyticus* on Experimental Myocardial Ischemia in Rats 2.1 Experimental Materials 2.1.1 Test Drug The three Bacterial agent groups in Example 1 were used as medicament in this example, and the manufacture and dosage of Bacterial agents were same as in Example 1. Meanwhile, FuFangDanshenPian was used as a control drug. Pituitrin, i.e., pituitrin injection, is produced by SHANGHAI No: 1 Biochemical Pharmaceutical Co., Ltd., with an approval number of H31022259 and a specification of 2 ml: 6 units.

2.1.2 Experimental Animals

Sprague-Dawley (SD) rats purchased from Guangdong Medical Laboratory Animal Center were used in the experiment. The SD rats were 6-week old rats and fed normally in the environment of Specific pathogen Free (SPF) level, in total of 70 rats.

2.1.3 Experimental Procedure

Effect of Acute Myocardial Ischemia in Rats Induced by Pituitrin

Fifty SD rats, half female and half male, weighing 180 to 220 g, were randomly divided into a model group, a FuFangDanShenPian group, bacterial agent group 1, bacterial agent group 2 and bacterial agent group 3, 10 rats for each group. The FuFangDanShenPian group and the bacterial agent groups were administered intragastrically once per day, in which the administration dosage for the FuFangDanShenPian group was 2 g/kg per day, and the administration dosage for the bacterial agent groups was 2 ml of bacterial solution in a bacteria concentration of $10^9$ cfu/ml; and the model group was administered with phosphate buffer saline (PBS) per day in a same amount, for 10 consecutive days. For each group, standard lead I electrocardiogram was recorded post 1 hour of last administration, followed by sublingual intravenous injection (iv.) with pituitrin in 1 unit/kg (in a volume of 1 ml/kg) within 15 seconds, after which the change of electrocardiogram was recorded post 5 seconds, 15 seconds, 30 seconds, 1 minute, 2 minutes, 3 minutes and 5 minutes, and the change of ST segment displacement before and after administration of pituitrin was measured and compared, with statistical analysis by using t test between groups. The specific experimental results are shown in Table 4.

TABLE 4

Effect of bacterial agent and FuFangDanShenPian on myocardial ischemia ST segment displacement of rat induced by pituitrin

| Experimental group(s) | ST displacement (mv) (±S) |
|---|---|
| Model group | 0.061 ± 0.012 |
| FuFangDanShenPian group | 0.032 ± 0.016* |
| Bacterial agent group 1 | 0.028 ± 0.009** |
| Bacterial agent group 2 | 0.027 ± 0.011** |
| Bacterial agent group 3 | 0.021 ± 0.012** |

According to the statistics in Table 4, the three bacterial agent groups provided in the present disclosure all can effectively reduce the myocardial ischemia ST segment displacement in rats relative to the model group (**P<0.01, *P<0.05), indicating that the bacterial agents provided in the present disclosure have an excellent relieving and protective effect on myocardial ischemia, the effect of which is superior than that of the FuFangDanShenPian group.

Example 3 Food Composition Containing *Bacteroides cellulosilyticus*

Raw materials were shown in Table 5.

TABLE 5

| Raw material(s) | Mass percentage (%) |
|---|---|
| bacteria component | 0.5 |
| milk | 90.0 |
| sugar | 9.0 |
| Vitamin C | 0.5 |

The bacteria components in formulas 1-3 were single bacteria components, respectively including *Bacteroides*

*cellulosilyticus* DSM 14838, *Bacteroides cellulosilyticus* CL02T12C19 and *Bacteroides cellulosilyticus* WH2, in which the formulas 1-3 refer to three formulas respectively containing a bacteria component, named as formula 1, formula 2 and formula 3.

Milk and sugar in proportion of formula as above were mixed, stirred to complete mixture, preheated, homogenized at the pressure of 20 Mpa, and then sterilized at about 90° C. for 5 to 10 minutes, cooled to 40 to 43° C., followed by adding a protective agent (Vitamin C) and inoculation of 1-100×10$^6$ cfu/g bacteria component, thus obtaining the food composition containing the bacterial component such as *Bacteroides cellulosilyticus*.

Example 4 Pharmaceutical Composition Containing *Bacteroides cellulosilyticus*

Raw materials were shown in Table 6.

TABLE 6

| Raw material(s) | Mass percentage (%) |
|---|---|
| bacteria component | 1.0% |
| lactose | 2.0% |
| yeast powder | 2.0% |
| peptone | 1.0% |
| purified water | 93.5% |
| vitamin C | 0.5% |

The bacteria components in formulas 1-3 were single bacteria components, respectively including *Bacteroides cellulosilyticus* DSM 14838, *Bacteroides cellulosilyticus* CL02T12C19 and *Bacteroides cellulosilyticus* WH2.

Lactose, yeast powder and peptone in proportion were mixed with purified water to be uniform, preheated to 60 to 65° C., homogenized at the pressure of 20 Mpa, and then sterilized at about 90° C. for 20 to 30 minutes, cooled to 36 to 38° C., followed by adding vitamin C and inoculation of 1-50×10$^6$ cfu/mL active strain *Bacteroides cellulosilyticus*, after which fermented at 36 to 38° C. to pH 6.0, centrifuged, freeze-dried to less than 3% of water content, thus obtaining a freeze-dried product containing bacteria component. 0.5 g of the freeze-dried product containing the bacteria component was weighed, mixed with an equal amount of maltodextrin and a protective agent (such as vitamin C), and then encapsulated into capsules, thus obtaining the pharmaceutical composition containing bacteria component such as *Bacteroides cellulosilyticus*.

Example 5 Manufacture of a Medicament Containing *Bacteroides cellulosilyticus* for Treating Lipid Metabolism Related Diseases (Such as Coronary Heart Disease)

5.1 Preparation of Bacterial Solution

*Bacteroides cellulosilyticus* (1×10$^9$ cfu/ml) were anaerobically fermented in the anaerobic PYG medium at 37° C. for 2 to 3 days.

5.2 Preparation of Growth Factors

The skimmed milk and casein were mixed, centrifuged and ultra-filtered to obtain a crude extract of milk growth factor, including nutrients of vitamins, purines and/or pyrimidines.

5.3 Manufacture of Medicament or Pharmaceutical Dosage Form 5 volumes (ml) of growth factor and 1 volume (ml) of protective agent (such as vitamin C) were added to 100 volumes (ml) of the fermented bacterial solution of *Bacteroides cellulosilyticus*, fully stirred to be uniform, and then added with starch excipients (such as maltodextrin), thus obtaining the medicament or pharmaceutical dosage form containing *Bacteroides cellulosilyticus*.

All publications mentioned herein are incorporated by reference as if each individual document was cited as a reference in the present application. It should also be understood that, after reading the above teachings of the present disclosure, those skilled in the art can make various changes or modifications, equivalents of which falls in the scope of claims as defined in the appended claims.

What is claimed is:

1. A method for treating lipid metabolism related diseases in a subject in need thereof, comprising administering to the subject a composition comprising a therapeutically effective amount of *Bacteroides cellulosilyticus*.

2. The method according to claim 1, wherein the lipid metabolism related diseases are selected from the group consisting of atherosclerosis related diseases, cardiovascular diseases, obesity and a combination thereof.

3. The method according to claim 1, wherein the *Bacteroides cellulosilyticus* is selected from the group consisting of *Bacteroides cellulosilyticus* DSM 14838, *Bacteroides cellulosilyticus* CL02T12C19, *Bacteroides cellulosilyticus* WH2 and a combination thereof.

4. The method according to claim 1, wherein the *Bacteroides cellulosilyticus* is capable of one or more effects selected from the group consisting of:
   (i) lowering blood lipid level in a mammal;
   (ii) reducing body weight of a mammal;
   (iii) relieving myocardial ischemia in a mammal; and
   (iv) alleviating vascular lesions in a mammal.

5. The method according to claim 1, wherein the *Bacteroides cellulosilyticus* or the composition is administrated orally.

6. The method according to claim 1, wherein the administration dosage is 0.01 to 5 g/50 kg body weight per day.

7. The method according to claim 1, wherein the subject is a human or non-human mammal, wherein the non-human mammal is a mouse, rat or primate.

8. The method according to claim 1, wherein the composition further comprises one or both of probiotics and prebiotics.

9. The method according to claim 8, wherein the probiotics are selected from the group consisting of Lactic acid bacteria, *Bifidobacteria, Lactobacillus acidophilus* and a combination thereof.

10. The method according to claim 8, wherein the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide and a combination thereof.

11. The method according to claim 1, wherein the composition further comprises a substance capable of maintaining the viability of *Bacteroides cellulosilyticus*.

12. The method according to claim 11, wherein the substance capable of maintaining the viability of *Bacteroides cellulosilyticus* is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E and a combination thereof.

13. The method according to claim 11, wherein the substance capable of maintaining the viability of *Bacteroides cellulosilyticus* is of a weight ratio (wt%) of 0.1% to 2%, based on the total weight of the composition.

14. The method according to claim 1, wherein the composition further contains a growth factor.

15. The method according to claim 1, wherein the composition contains $1\times10\text{-}1\times10^{15}$ cfu/mL or cfu/g of *Bacteroides cellulosilyticus*, based on the total volume or total weight of the composition.

16. The method according to claim 1, wherein the composition is in a unit dosage form selected from the group consisting of one tablet, one capsule and one vial, and wherein the composition in each unit dosage form is of a mass of 0.05 g to 5 g.

17. The method according to claim 2, wherein the atherosclerosis related diseases are selected from the group consisting of coronary heart disease, coronary artery disease (CAD), atherosclerotic heart disease, atherosclerotic cardiovascular diseases, ischemic heart disease and a combination thereof.

18. The method according to claim 1, wherein the composition further comprises a food acceptable or pharmaceutically acceptable carrier.

19. The method according to claim 18, wherein the food acceptable or pharmaceutically acceptable carrier comprises excipient, lubricant, wetting agent, emulsifier, suspension stabilizer, preservative, sweetener or flavor.

20. The method according to claim 1, wherein the composition is a food composition, a health care composition, a pharmaceutical composition, a beverage composition, a feed composition or a combination thereof,
   wherein the composition is of a dosage form selected from the group consisting of powder, pulvis, tablet, sugar coating agent, capsule, granule, suspension, solution, syrup, drop and sublingual tablet.

* * * * *